US007884071B2

(12) United States Patent
Bauer et al.

(10) Patent No.: US 7,884,071 B2
(45) Date of Patent: Feb. 8, 2011

(54) ADMINISTRATION FORM FOR PHARMACEUTICALLY ACTIVE PEPTIDES WITH SUSTAINED RELEASE AND METHOD FOR THE PRODUCTION THEREOF

(75) Inventors: Horst Bauer, Hersbruck (DE); Thomas Reissmann, Frankfurt am Main (DE); Peter Romeis, Gelnhausen (DE); Berthold Roessler, Brandenburg (DE)

(73) Assignee: Zentaris GmbH, Frankfurt am Main (DE)

( * ) Notice: Subject to any disclaimer, the term of this patent is extended or adjusted under 35 U.S.C. 154(b) by 62 days.

(21) Appl. No.: 10/529,203

(22) PCT Filed: Sep. 26, 2003

(86) PCT No.: PCT/EP03/10732

§ 371 (c)(1),
(2), (4) Date: Mar. 25, 2005

(87) PCT Pub. No.: WO2004/030650

PCT Pub. Date: Apr. 15, 2004

(65) Prior Publication Data

US 2005/0282731 A1 Dec. 22, 2005

Related U.S. Application Data

(60) Provisional application No. 60/414,225, filed on Sep. 27, 2002.

(30) Foreign Application Priority Data

Sep. 27, 2002 (DE) ................. 102 45 525
Apr. 26, 2003 (DE) ................. 103 20 051

(51) Int. Cl.
*A61K 38/22* (2006.01)
*C07K 14/575* (2006.01)
*C07K 14/59* (2006.01)

(52) U.S. Cl. ............... 514/9.7; 514/1.1; 514/10.1; 514/10.3; 514/19.3; 514/19.4; 514/19.5; 530/388.24; 530/399

(58) Field of Classification Search ................. None
See application file for complete search history.

(56) References Cited

U.S. PATENT DOCUMENTS

| 5,411,951 A | 5/1995 | Mitchell |
| 5,595,760 A | 1/1997 | Cherif-Cheikh |
| 5,663,145 A * | 9/1997 | Engel et al. ............ 514/15 |
| 5,916,582 A | 6/1999 | Stevenson et al. |
| 5,942,493 A * | 8/1999 | Kutscher et al. ........... 514/15 |
| 6,180,608 B1 * | 1/2001 | Gefter et al. ............ 514/13 |
| 6,503,534 B1 | 1/2003 | Pellet et al. |
| 6,716,817 B1 | 4/2004 | Engel et al. |
| 6,828,415 B2 | 12/2004 | Engel et al. |
| 6,863,891 B2 | 3/2005 | Engel et al. |
| 6,867,191 B2 | 3/2005 | Engel et al. |
| 7,005,418 B1 * | 2/2006 | Riethmuller-Winzen et al. ............ 514/12 |
| 2002/0039996 A1 | 4/2002 | Bauer et al. |
| 2002/0065226 A1 | 5/2002 | Siler-Khodr |

FOREIGN PATENT DOCUMENTS

| AO | 0 510 913 | 10/1992 |
| CN | 1348462 A | 5/2002 |
| RU | 2 145 234 | 2/2000 |
| WO | 99/48517 | 9/1999 |
| WO | WO 00/55190 | 9/2000 |

OTHER PUBLICATIONS

Jiang, Guangcheng et al. "Betidamino Acid Scan of the GnRH Antagonist Acyline", J. Med. Chem., vol. 40, pp. 3739-3748, XP002071836 1997.

Mizuguchi, K. et al. "Phase III clinical trial of ICI 118,630(Zoladex) depot for hysteromyoma. Randomized non-blind comparative test using symptomatic treatment as a control", Sanfujinka no Sekal. vol. 47, pp. 229-257, English abstract only, STN Search 1995.

"Information to supplement the report on endometriosis", http://www.wdr.de/tv/frautv/archiv2001/f21060_e.html, with English translation 2001.

"Hormones and antihormones", Excerpts from Handbuch Medikamente, 3rd edition, http://home.t-online/home/koubenec/brustkrebs-therapie/chemo-hormone.htm., with English translation 2000.

Schwarz, H. P. "Do all forms of precocious puberty require treatment?", Scientific Meeting of the Working Group on the Occasion of the 54th Congress of the German Society of Gynecology and Obstetrics (DGGG), http://www.kindergynaekologie.de/html/themen.html., with English translation 2002.

* cited by examiner

*Primary Examiner*—Julie Ha
(74) *Attorney, Agent, or Firm*—Oblon, Spivak, McClelland, Maier & Neustadt, L.L.P.

(57) ABSTRACT

The invention relates to pharmaceutical administration forms with sustained release comprising at least one pharmacologically active peptide. The invention also relates to a method for the production thereof, a kit comprising a lyophilised peptide and an aqueous solution of an inorganic salt or acetic acid salt and the use of an aqueous solution of an inorganic or acetic acid salt for producing a pharmaceutical administration form which releases peptides in a continuous manner over a long period of time.

33 Claims, 6 Drawing Sheets

Figures

Fig. 1 (cf. example 3): Dose-dependent suppression of testosterone levels by D-63153 depot in male rats, 5-25 mg/kg i.m., averages Fig. 2 (cf. example 5): Representation of the dependence of the viscosity of D-63153 preparation on the solvent used (viscosity was determined using a falling sphere micro-viscometer)

Fig. 6: Physicochemical data on D-63 153
Sequence: Ac-D-Nal(2)-D-Cpa-D-Pal(3)-Ser-N-Me-Tyr-D-Hci-Nle-Arg-Pro-D-Ala-NH2
Name: D-63153 (e.g. acetate salt)
Structural formula:
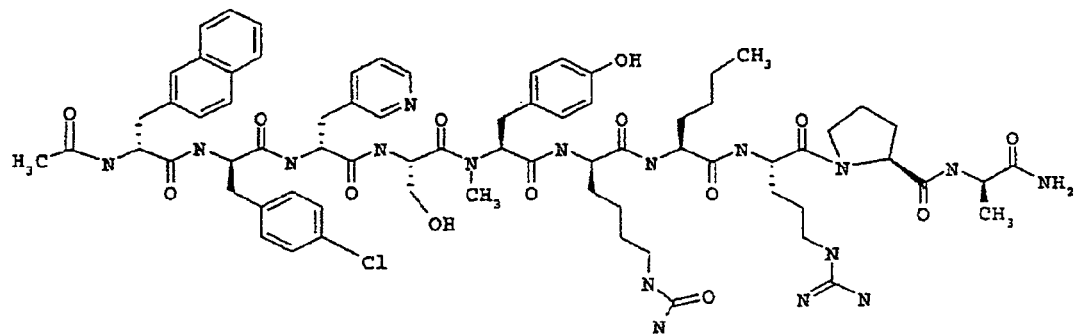
Molecular formula: $C_{72} H_{96} Cl N_{17} O_{14} \times C_2 H_4 O_2$
Molecular weight: 1459.1 g/mole (free base)
Spec. optical rotation: −47.0 to −57.0 (0.25% in MeOH)
Solubility: 0.75 mg/ml in water
Appearance: white amorphous powder, odorless

ADMINISTRATION FORM FOR PHARMACEUTICALLY ACTIVE PEPTIDES WITH SUSTAINED RELEASE AND METHOD FOR THE PRODUCTION THEREOF

FIELD OF THE INVENTION

The invention relates to pharmaceutical administration forms with sustained release of active ingredient having at least one pharmacologically active peptide, to a method for the production thereof, to a kit including a lyophilized peptide and an aqueous solution of an inorganic salt or acetic acid salt and to the use of an aqueous solution of an inorganic or acetic acid salt for producing a pharmaceutical administration form which displays sustained peptide release over a prolonged period.

DESCRIPTION OF THE PRIOR ART

The following pharmaceutical administration forms with sustained release of the pharmaceutically active peptide are known in the art:
1. Pharmaceutical administration forms with micro-encapsulated and/or incorporated and/or conjugated pharmaceutically active peptides in a biodegradable polymeric matrix (e.g. described in: Maulding, H. V., J. Controlled Release (1987), 6, 167-76; Siegel, R. A., Langer, R. Pharm. Res. (1984), 1, 2-10; Patent WO 9832423, Patent WO 2001078687).
2. Pharmaceutical administration forms including from scarcely water-soluble complexes of the pharmaceutically active peptide and an organic carrier molecule, such as, for example, polysaccharides (e.g. described in: Patent WO 2000047234).

In both cases, enzymatic degradation of matrix or complex leads to the sustained release of the peptide.

PROBLEMS ASSOCIATED WITH THE PRIOR ART

Production of the known microcapsules or particles and insoluble complexes of the peptide compounds require very demanding procedures in order to obtain administration forms with sustained release of active ingredient. Normally, insoluble or slightly soluble compounds are produced through precipitation of the peptide compound with the counterion. The precipitate is collected by filtration and centrifugation, washed with water and dried. In most cases, the solid material is then powdered. All the individual steps in the production method must be carried out under GMP conditions in an aseptic working area in order to make it possible in this way to guarantee the sterility of the final product.

In the procedures for producing microcapsules, more or less toxic organic solvents are used in order to dissolve the biodegradable polymer matrix. The dissolved active substance and the polymers of the matrix are then emulsified. After evaporation of the organic solvent, the particles or the microcapsules are separated, washed and dried.

DESCRIPTION OF THE INVENTION

It has now surprisingly been found that administration forms with sustained release of active ingredient for pharmaceutically active peptides are obtained by reconstituting a lyophilized peptide compound with a low-concentration inorganic salt solution before administration, with the amount of lyophilized peptide compound being chosen so that the peptide solution or suspension after reconstitution is highly concentrated. As a possible explanation, it is presumed that under these conditions there is controlled development of aggregates of the peptide compounds, which shows or show delayed dissolution. The result is then the found sustained release of this active ingredient into the circulation. In this case, the formation of the aggregates leads to a colloidal dispersion whose viscosity are influenced by the concentration of the peptide compound, the salt concentration and the standing time after reconstitution.

BRIEF DESCRIPTION OF THE DRAWINGS

A more complete appreciation of the invention and many of the attendant advantages thereof will be readily obtained as the same becomes better understood by reference to the following Figures in conjunction with the detailed description below.

FIG. 6 shows the physicochemical date on D-63153, including: the sequence, the name, the structural formula, the molecular formula, the molecular weight, the spectral optical rotation, the solubility, and the appearance.

DETAILED DESCRIPTION OF THE INVENTION

Figure 1:
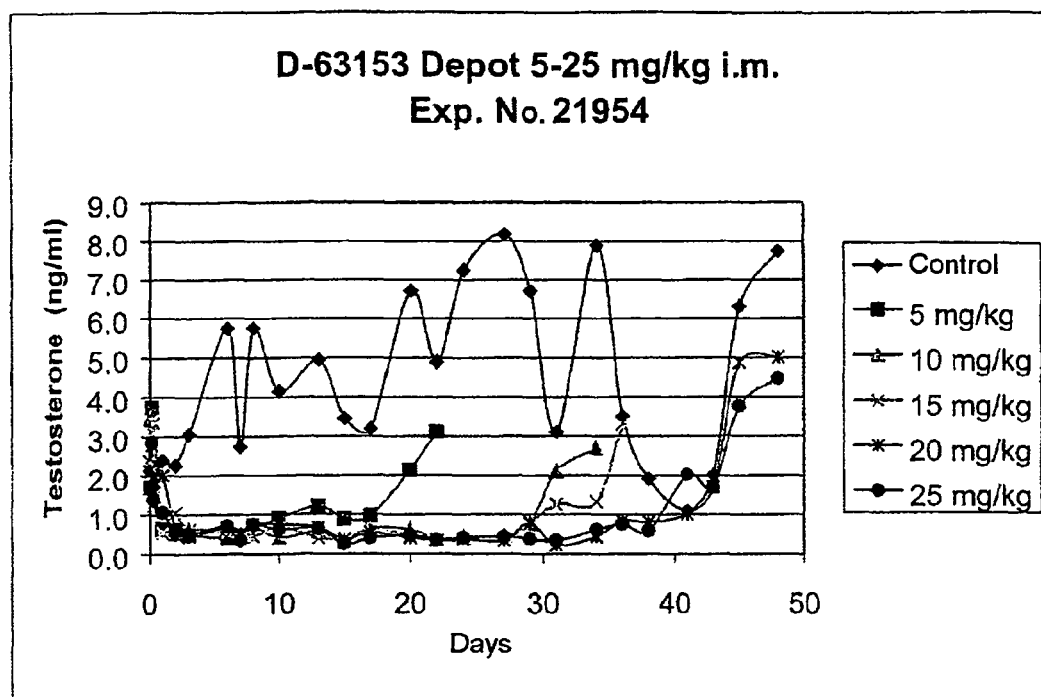
FIG. 1 shows a dose-dependent suppression of the testosterone levels by D-63153 depot in male rates, 5-25 mg/kg i.m., averages, as described in Example 3.

According to the present invention, a pharmaceutical gel preparation including at least one pharmaceutically active ionic peptide compound mixed in a predetermined amount of the value $X_{optimum}$ (in mg of peptide per ml of the preparation) with an aqueous solution of an inorganic or acetic acid salt in a predetermined concentration of the value $Y_{optimum}$ (in % weight/volume), and after the mixing the administration can take place immediately, or a standing time of up to about 120 minutes to be observed, and it being possible for the value $X_{optimum}$ to be selected by a test method A including the stages of administration of various amounts $X_n$ (number of different amounts n, where n≧1) (in mg) of the peptide as a mixture with an isotonic aqueous solution of mannitol onto or to a test system and selection of the amount $X_{optimum}$ (in mg of peptide per ml of mixture) which provided in the experiment the most favorable blood plasma levels of the peptide in the test system in relation to $C_{max}$ (maximum blood plasma concentration) and $t_{max}$ (time until $C_{max}$ is reached), and the concentration $Y_{optimum}$ being selected by a test method B including the stages of administration of the amount $X_{optimum}$ (in mg of peptide per ml of mixture) of the peptide as a mixture with aqueous solutions which differ in the concentration $Y_n$ (number of different concentrations n, where n≧1) (in % weight/volume) onto or to a test system and selection of the concentration $Y_{optimum}$ (in % weight/volume) was fixed as the concentration which in the experiment resulted in the highest value for the plasma concentration $C_{active}$, where ($C_{min}$=lowest plasma concentration of the peptide at which the peptide still has an adequate pharmaceutical effect in the experiment). At the same time, it has an influence on the time $t_{active}$ until the highest concentration in the plasma is reached, where $t_{active} > t_{max}$, provided.

A further embodiment provides a pharmaceutical preparation characterized in that the pharmaceutically active ionic peptide compound is cationic.

A further embodiment provides a pharmaceutical preparation characterized in that the pharmaceutically active ionic peptide compound is anionic.

A further embodiment provides a pharmaceutical preparation characterized in that the pharmaceutically active ionic peptide compound is a mono-, di- or multivalent cationic or anionic peptide.

A further embodiment provides a pharmaceutical preparation characterized in that the pharmaceutically active ionic peptide compound is a mono-, di- or multivalent ampholytic peptide.

A further embodiment provides a pharmaceutical preparation characterized in that the pharmaceutically active ionic peptide compound has a length of from 5 to 20 amino acids.

A further embodiment provides a pharmaceutical preparation characterized in that the pharmaceutically active ionic peptide compound has a length of from 8 to 12 amino acids.

A further embodiment provides a pharmaceutical preparation characterized in that the pharmaceutically active ionic peptide compound is a GnRH analog.

A further embodiment provides a pharmaceutical preparation characterized in that the pharmaceutically active ionic peptide compound is a GnRH antagonist.

A further embodiment provides a pharmaceutical preparation characterized in that the pharmaceutically active ionic peptide compound has been selected from the group consisting of cetrorelix, teverelix, abarelix, ganirelix, azaline B, antide, detirelix, ramorelix, degarelix, D-63153 or their pharmaceutically active salt or mixtures thereof.

A further embodiment provides a pharmaceutical preparation characterized in that the pharmaceutically active ionic peptide compound is the GnRH antagonist D-63153.

A further embodiment provides a pharmaceutical preparation characterized in that the inorganic salt or the acetic acid salt is a physiologically tolerated salt.

A further embodiment provides a pharmaceutical preparation characterized in that aqueous inorganic salt or acetic acid salt has been selected from the group consisting of sodium chloride, calcium chloride, magnesium chloride, sodium acetate, calcium acetate and magnesium acetate.

A further embodiment provides a pharmaceutical preparation characterized in that the mixture of the pharmaceutically active ionic peptide compound and the aqueous solution of the inorganic salt or of the acetic acid salt is a liquid suspension or a semisolid dispersion.

A further embodiment provides a pharmaceutical preparation characterized in that the amount X of the pharmaceutically active ionic peptide compound is in the range from about 5 to about 50 mg per ml of the total amount of the pharmaceutical preparation.

A further embodiment provides a pharmaceutical preparation characterized in that the amount X of the pharmaceutically active ionic peptide compound is in the range from about 10 to about 50 mg per ml of the total amount of the pharmaceutical preparation.

A further embodiment provides a pharmaceutical preparation characterized in that the amount X of the pharmaceutically active ionic peptide compound is in the range from about 20 to about 30 mg per ml of the total amount of the pharmaceutical preparation.

A further embodiment provides a pharmaceutical preparation characterized in that the amount X of the pharmaceutically active ionic peptide compound is in the range from about 25 mg per ml of the total amount of the pharmaceutical preparation.

A further embodiment provides a pharmaceutical preparation characterized in that D-63153 is the pharmaceutically active ionic peptide compound, and the amount X is in the range from about 5 to about 50 mg per ml of the total amount of the pharmaceutical preparation.

A further embodiment provides a pharmaceutical preparation characterized in that D-63153 is the pharmaceutically active ionic peptide compound, and the amount X is in the range from about 10 to about 50 mg per ml of the total amount of the pharmaceutical preparation.

A further embodiment provides a pharmaceutical preparation characterized in that D-63153 is the pharmaceutically active ionic peptide compound, and the amount X is in the range from about 20 to about 30 mg per ml of the total amount of the pharmaceutical preparation.

A further embodiment provides a pharmaceutical preparation characterized in that D-63153 is the pharmaceutically active ionic peptide compound, and the amount X is in the region of about 25 mg per ml of the total amount of the pharmaceutical preparation.

A further embodiment provides a pharmaceutical preparation characterized in that the concentration Y of the aqueous inorganic or acetic acid salt solution is equal to or less than 0.9% (weight/volume).

A further embodiment provides a pharmaceutical preparation characterized in that the concentration Y of the aqueous inorganic or acetic acid salt solution is in the range from about 0.01% to about 0.9% (weight/volume).

A further embodiment provides a pharmaceutical preparation characterized in that the concentration Y of the aqueous inorganic or acetic acid salt solution is in the range from about 0.05% to about 0.5% (weight/volume).

A further embodiment provides a pharmaceutical preparation characterized in that the concentration Y of the aqueous inorganic or acetic acid salt solution is about 0.1% (weight/volume).

A further embodiment provides a pharmaceutical preparation characterized in that the inorganic salt is sodium chloride and in that the concentration Y is equal to or less than about 0.9% (weight/volume).

A further embodiment provides a pharmaceutical preparation characterized in that the inorganic salt is sodium chloride and in that the concentration Y is in the range from about 0.01% to about 0.9% (weight/volume).

A further embodiment provides a pharmaceutical preparation characterized in that the inorganic salt is sodium chloride and in that the concentration Y is in the range from about 0.05% to about 0.5% (weight/volume).

A further embodiment provides a pharmaceutical preparation characterized in that the inorganic salt is sodium chloride and in that the concentration Y is about 0.1% (weight/volume).

A further embodiment provides a pharmaceutical preparation characterized in that at least one of the pharmaceutically active ionic peptide compound is D-63153, and the inorganic salt is sodium chloride.

A further embodiment provides a pharmaceutical preparation characterized in that at least one of the pharmaceutically active ionic peptide compound is D-63153, and the amount X thereof is about 25 ml per ml of the preparation, and in that the inorganic salt is sodium chloride, and the concentration Y thereof is about 0.1% (weight/volume).

A further aspect of the invention provides a method for producing a pharmaceutical preparation including the steps A) bringing together an amount $X_{optimum}$ (in mg per ml of the finished preparation) of at least one pharmaceutically active peptide compound in lyophilized form and an aqueous solution of an inorganic or acetic acid salt in a concentration with the value $Y_{optimum}$ (% weight/volume) and A) mixing the components.

A further embodiment of the invention provides a method for producing a pharmaceutical preparation, characterized in that the pharmaceutically active ionic peptide compound is D-63153, and the inorganic salt is sodium chloride.

A further embodiment of the invention provides a method for producing a pharmaceutical preparation, characterized in that the pharmaceutically active ionic peptide compound is D-63153, and the amount thereof is about 25 mg/ml, and in that the organic salt is sodium chloride, and the concentration thereof is about 0.1% (weight/volume).

A further embodiment of the invention provides a method for producing a pharmaceutical preparation, characterized by further including the step of sterilization of the peptide formulation by irradiation with gamma rays or electron beams takes place.

A further embodiment of the invention provides a method for producing a pharmaceutical preparation, characterized in that the production of the peptide formulation takes place with use of aseptic procedures.

A further aspect of the invention provides a kit for producing a pharmaceutical preparation, including a previously fixed amount X (in mg per ml of the finished preparation) of a pharmaceutically active ionic peptide compound in lyophilized form and of an aqueous solution of an inorganic or acetic acid salt in a previously fixed concentration Y % (weight/volume).

A further embodiment of the invention provides a kit for producing a pharmaceutical preparation, characterized in that the pharmaceutically active peptide compound is D-63153 in lyophilized form.

A further embodiment of the invention provides a kit for producing a pharmaceutical preparation, characterized in that the D-63153 lyophilizate additionally comprises mannitol.

A further embodiment of the invention provides a kit for producing a pharmaceutical preparation, characterized in that the inorganic salt is sodium chloride.

A further embodiment of the invention provides a kit for producing a pharmaceutical preparation, characterized in that the amount X of D-63153 is about 25 mg per finished preparation and the concentration of the aqueous sodium chloride solution is about 0.1% weight/volume.

A further aspect of the invention provides a method for treating a patient with a pharmaceutically active peptide compound, characterized in that a pharmaceutical preparation as claimed in any of the aforementioned claims is administered subcutaneously or intramuscularly to the patient by means of a syringe.

A further embodiment of the invention provides a method for treating a patient with a pharmaceutically active peptide compound, characterized in that the administered pharmaceutical preparation displays a sustained pharmaceutical activity.

A further embodiment of the invention provides a method for treating a patient with a pharmaceutically active peptide compound, characterized in that the administered pharmaceutical preparation displays a sustained pharmaceutical activity for at least 4 weeks.

A further embodiment of the invention provides a method for treating a patient with a pharmaceutically active peptide compound, characterized in that the administered pharmaceutical preparation displays a sustained pharmaceutical activity for at least 8 weeks.

A further embodiment of the invention provides a method for treating a patient with a pharmaceutically active peptide compound, characterized in that the administered pharmaceutical preparation displays a sustained pharmaceutical activity for at least 12 weeks.

A further embodiment of the invention provides a method for treating a hormone-dependent disorder of a patient by subcutaneous or intramuscular administration of the aforementioned pharmaceutical preparations in a patient requiring this.

A further aspect of the invention provides a method for treating prostate cancer in a patient by subcutaneous or intramuscular administration of the pharmaceutical preparation of the invention described above to a patient requiring this.

A further aspect of the invention provides a method for treating breast cancer in a patient by subcutaneous or intramuscular administration of the pharmaceutical preparation of the invention described above to a patient requiring this.

A further aspect of the invention provides a method for treating uterine myomas in a patient by subcutaneous or intramuscular administration of the pharmaceutical preparation of the invention described above to a patient requiring this.

A further aspect of the invention provides a method for treating endometriosis in a patient by subcutaneous or intramuscular administration of the pharmaceutical preparation of the invention described above to a patient requiring this.

A further aspect of the invention provides a method for treating precocious puberty in a patient by subcutaneous or intramuscular administration of the pharmaceutical preparation of the invention described above to a patient requiring this.

A further aspect of the invention provides a method for modifying the reproductive function in a patient by subcutaneous or intramuscular administration of the pharmaceutical preparation of the invention described above to a patient requiring this.

A further aspect of the invention provides a pharmaceutical preparation, characterized in that the mixture of the pharmaceutically active ionic peptide compound and of the aqueous solution of the inorganic salt or of the acetic acid salt is a molecular-dispersed or colloidal mixture which may be of liquid to semisolid consistency.

A further aspect of the invention provides a pharmaceutical preparation, characterized in that a colloidal dispersion is formed by reconstitution.

A further aspect of the invention provides a pharmaceutical preparation, characterized in that a colloidal dispersion is formed by storage or leaving to stand after reconstitution and changes its viscosity as a function of time and thus improves the reproducibility of the delayed release of active ingredient.

A further aspect of the invention provides a kit including a lyophilized pharmaceutically active peptide, for example D-63153, where appropriate together with one or more pharmaceutically acceptable excipients or additives, and a low-concentration aqueous solution of an inorganic salt, preferably sodium chloride.

In a preferred embodiment, the peptide compound of the administration form is a GnRH analog, even better a GnRH antagonist, and the inorganic salt is a highly soluble physiological salt, preferably sodium chloride. Because of the parenteral administration, it is necessary for the powdered peptide compound and the solution for the reconstitution to be sterile.

The present invention makes it possible easily to produce suspensions with sustained release of a peptide compound active ingredient, preferably of a GnRH antagonist. This is obtained by reconstituting a highly concentrated lyophilizate of the peptide compound comprising mannitol with a dilute inorganic salt solution (e.g. sodium chloride solution).

Formation of the pharmaceutical formulation of the invention is moreover dependent on the following parameters:
1. the concentration of the peptide compound in the solution after reconstitution
2. the concentration of the inorganic salt in the solvent employed for reconstitution
3. the standing time of the solution after reconstitution and the extent of aggregation obtained thereby, which is reflected by the viscosity increase.

The high concentration of the peptide compound leads to aggregation thereof, which can be controlled by adding an inorganic salt solution. The solubility of the peptide compound decreases as the salt concentration increases. The colloidal properties become more prominent than the solution properties, as is clear from the increasing viscosity even as far as a gel. The "gel" in this connection represents a bicoherent system consisting of the peptide aggregate as the solid phase and water as the liquid phase.

The administration forms of the invention for pharmaceutically active peptides with sustained release of active ingredient are always in the form of a gel before administration.

In an ideal range of salt concentration, combined with a suitable amount of peptide compounds, sustained release of active ingredient can be obtained for a period of 4 weeks or more.

Any physiologically tolerated inorganic salt can be used for the inorganic salt solution, preferably sodium chloride.

The reconstitution takes place with a low-concentration salt solution. The concentration should in this case be equal to or less than about 0.9% (weight/volume), preferably in the range from about 0.01% to about 0.9%, particularly preferably in the range from about 0.05 to about 0.5% (weight/volume), very preferably about 0.1% (weight/volume).

A low-concentration sodium chloride solution with a sodium chloride concentration in the range from about 0.05 to about 0.5% (weight/volume), preferably of about 0.1% (weight/volume) is preferred.

The peptide in the formulation is a pharmacologically active peptide compound which may be a mono-, di- or multivalent cationic or anionic peptide. The peptide may consist of from 5 to 20 amino acids in length, more preferably from 8 to 12 amino acids in length. More in detail, the peptide compound is a GnRH analog and the GnRH analog is a GnRH antagonist. Examples of GnRH analogs are cetrorelix, teverelix (Deghenghi et al., Biomed & Pharmacother 1993, 47, 107), abarelix (Molineaux et al., Molecular Urology 1998, 2, 265), ganirelix (Nestor et al., J. Med. Chem. 1992, 35, 3942), azaline B, antide, A-75998 (Cannon et al., J. Pharm. Sci. 1995, 84, 953), detirelix (Andreyko et al., J. Clin. Endocrinol. Metab. 1992, 74, 399), RS-68439, ramorelix (Stockemann and Sandow, J. Cancer Res. Clin. Oncol. 1993, 119, 457), degarelix (Broqua, P.: Riviere et al., JPET 301, 95), D-63153 (PCT: EP00/02165).

The structures of the abovementioned GnRH analogs are depicted for example in the abovementioned references and in the following review articles: Behre et al., GnRH antagonists: an overview, Proceedings of the 2nd World Conference on Ovulation Induction, The Parthenon Publishing Group Ltd, UK; Kutscher et al., Angew. Chem. 1997, 109, 2240.

The compound D-63 153 is described inter alia in German patent application No. DE 199 11 771.3. The physico-chemical data are summarized in FIG. 6.

The concentration of the pharmaceutically active peptide may be in the range from about 5 mg/ml to about 50 mg/ml, preferably about 10 mg/ml to about 50 mg/ml, particularly preferably about 20 mg/ml to about 30 mg/ml and very particularly preferably about 25 mg/ml (ml=total volume of the finished administration form).

All pharmaceutically active peptides can be employed in the concentrations mentioned. The peptide D-63 153 is particularly preferred.

A further aspect of the present invention provides a method for producing administration forms for pharmaceutically active peptides with sustained release of active ingredient.

According to the invention, the acetate salt base of the peptide compound is completely dissolved in aqueous acetic acid until a clear solution is formed. The solution is diluted with water for injections, which receives the necessary amount of mannitol so that an isotonic solution which can be administered is formed. After sterilizing filtration of the solution it is dispensed into vials and lyophilized.

A sodium chloride solution (e.g. 0.1%) is used for reconstitution before administration in order thus to control the aggregation of the peptide and therefore also the solubility. The reconstitution takes place where appropriate by careful swirling or shaking, it being necessary to avoid foaming.

The pharmaceutical administration forms of the invention permit sustained delivery of the peptide compound after administration of the administration form in the subject. The duration and extent of delivery can be varied by changing the concentrations of peptide compound and the concentration of the salt used.

The standing time after reconstitution is also important for the release of the peptide active ingredient. The standing time may be between about 0 to about 120 min, preferably between about 10 to about 120 minutes, particularly preferably between about 15 to 60 minutes. It has been found that the colloidal system obtained by aggregation changes during the standing time, and that the viscosity increases. With a standing time of more than about 120 min, no significant further change in the viscosity was to be observed.

The pharmaceutical administration forms of the invention can preferably be administered subcutaneously (s.c.) or intramuscularly (i.m.). In the case of intramuscular administration, the injection takes place for example into the gluteus maximus muscle, preferably into the upper outer quadrant of the gluteus maximus muscle. In the case of subcutaneous administration, the injection takes place for example into the subcutis of the abdomen.

The present invention is described in detail in examples 1 to 7 below without restricting the invention thereto.

Example 1

200 g of pure D-63153 (calculated as free base) are dissolved in 3386.7 g of 30% strength aqueous acetic acid to form a clear solution. 438.4 g of mannitol is added and dissolved by stirring. The solution is made up to a total amount of 20 320 g with water for injections.

After the solution has been sterilized by filtration it is dispensed in 10 ml portions into vials for lyophilization.

After the method, each vial contains 100 mg of D-63153 (free base) and 109.6 mg of mannitol.

The lyophilizate is reconstituted by adding 4 ml of 0.1% strength sodium chloride solution and carefully shaking (avoid foaming) in order to obtain a suspension of 25 mg/ml.

Example 2

Lyophilizates which contain 75 mg of D-63153 were produced and reconstituted with 3 ml of solvent (25 mg of D-63153/ml). The reconstitution took place with sterile water for injections (non-depot administration form; see table 1) or with 0.1% NaCl (depot administration form; see table 2). A single dose of 1.68 mg/kg was injected subcutaneously into beagle dogs. The D-63153 plasma levels were measured at various times after administration.

It was possible through the use of the depot administration form to reduce the maximum plasma levels (Cmax), while the area under the curve remained substantially stably maintained, which results in a depot effect. The absolute bioavailability remained substantially unchanged and was calculated to be 62% for the non-depot administration form, and 64.3% for the depot form [Schwahn and Romeis, 1999].

Example 3

In order to subrime the D-63153 depot for its testosterone-suppressing potential, it was injected in 5 different doses (5-25 mg/kg) intramuscularly (i.m.) into male rats. The depot administration form was generated by resuspending D-63153 lyophilizate in 0.1% strength sterile NaCl. The testosterone level was measured before administering the medicament and in each case 4 hours, 8 hours and 24 hours thereafter. In addition, the testosterone level was determined once a day in the first week after injection and subsequently on every 2nd day, in each case until the testosterone level was again in the normal range. The control group was treated only with a vehicle solution (see FIG. 1). A dose-dependent suppression of the testosterone levels was detectable in all groups. The suppression lasted for from 17 days (5 mg/kg) to 43 days (20 mg/kg). The testosterone levels were subsequently again within the normal range within a few days.

Example 4

10 mg lyophilizates of D-63153 were reconstituted in 4 ml of sterile water for injections (non-depot administration form, 2.5 mg/ml D-63153, clinical phase 1a) and 100 mg lyophilizates of D-63153 were dissolved in 4 ml of 0.1% NaCl (depot administration form, 25 mg/ml D-63153, clinical phase 1b). Volunteer male test subjects received intramuscular injections of 10 mg per person. The D-63153 plasma levels were measured at various times after administration (see table 3).

The results show that the depot effect can be confirmed both through lower $C_{max}$ and $AUCO_{0-24}$ plasma levels and through a prolongation of $t_{max}$, $t_{1/2}$ and in particular an increase in the MRT (mean residence time). The depot administration form has almost the same $AUC_{0-tlast}$ as the non-depot administration form (887.44 ng*h/ml compared with 1165.93 ng*h/ml), thus showing that the two compositions have similar bioavailabilities. Release is slower from the depot administration form, indicated by a lower $c_{max}$ level and a value for MRT which is more than twice as high.

Example 5

Figure 2:
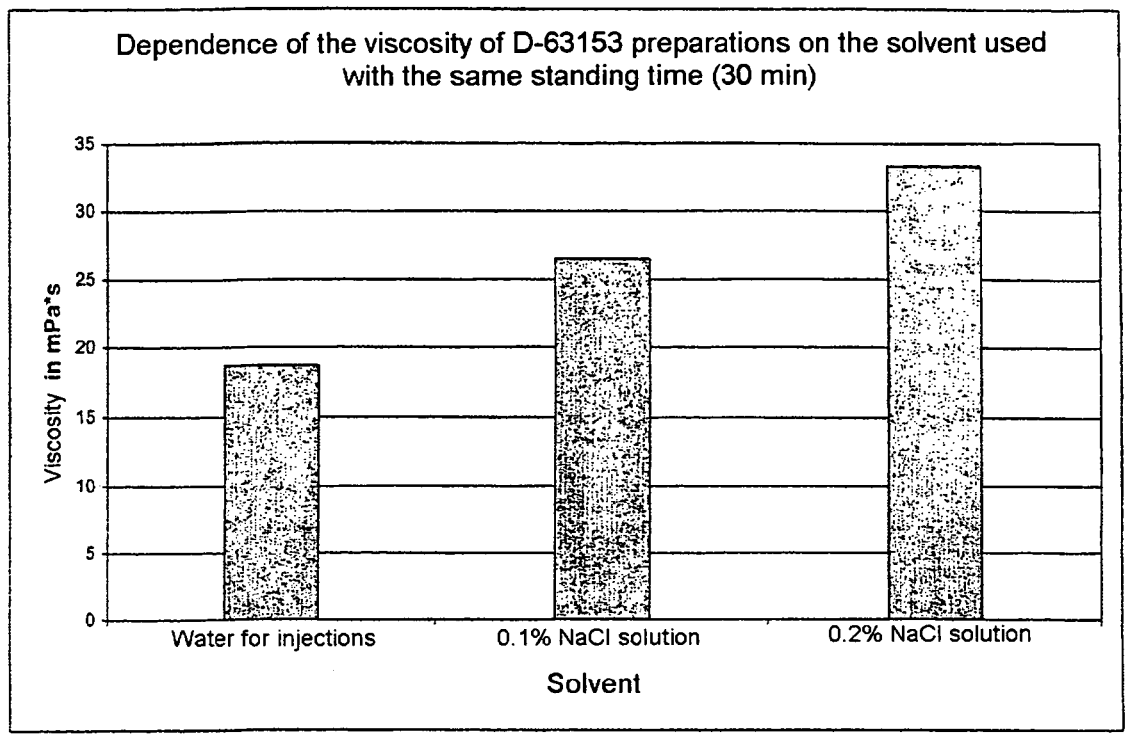
FIG. 2 shows a representation of the dependence of the viscosity of D-63153 preparation on the solvent used (viscosity was determined using a falling sphere micro-viscometer) as described in Example 5.

Lyophilizates containing 65 mg and 100 mg of D-63153 were produced and reconstituted with solvent to result in a solution which has a concentration of 25 mg of D-63153/ml. The solvents used were water for injections, 0.1% NaCl solution and 0.2% NaCl solution. The extent of the changes in the colloidal properties of the solutions was investigated by means of the viscosities thereof. The results are summarized in FIG. 2.

Example 6

Figure 3:
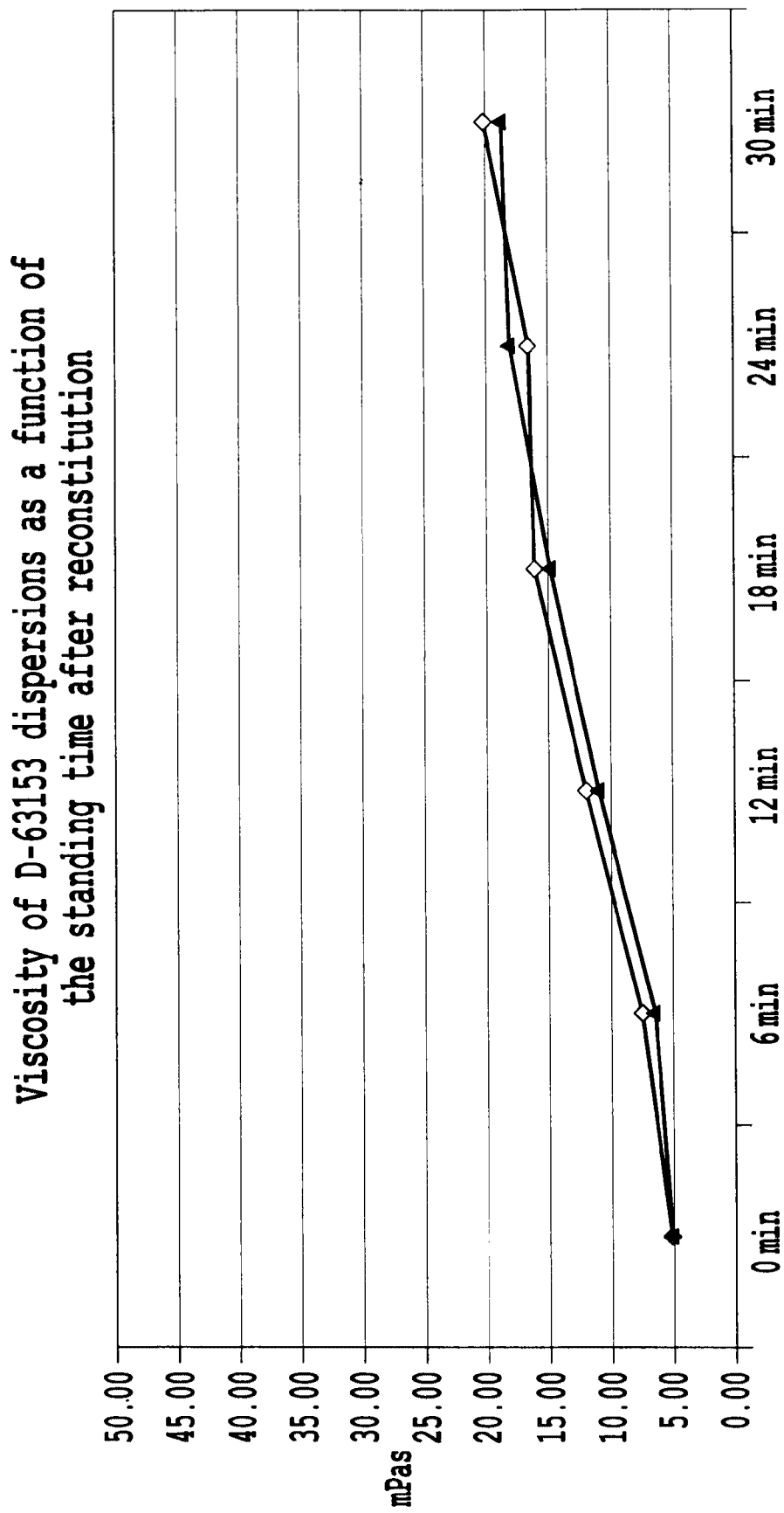
FIG. 3 shows a representation of the connection between viscosity of the peptide preparation and the standing time after reconstitutions (viscosity was determined using a falling sphere micro-viscometer) as described in Example 6. According to Example 6, two lyophilizate products containing 100 mg of D-63153 in each case were reconstituted with the same solvent to have a concentration of 25 mg/mL. Thus, the two data sets in FIG. 3 represent duplicate experiments showing that both traces of viscosity in the diagram have an excellent overlap without straggling.

Lyophilizates containing 100 mg of D-63153 were produced and reconstituted with solvent to result in a solution which has a concentration of 25 mg/ml. To describe the change in the colloidal system that arises after reconstitution, FIG. 3 depicts the viscosity as a function of the standing time or storage time after reconstitution.

Example 7

Figure 4:
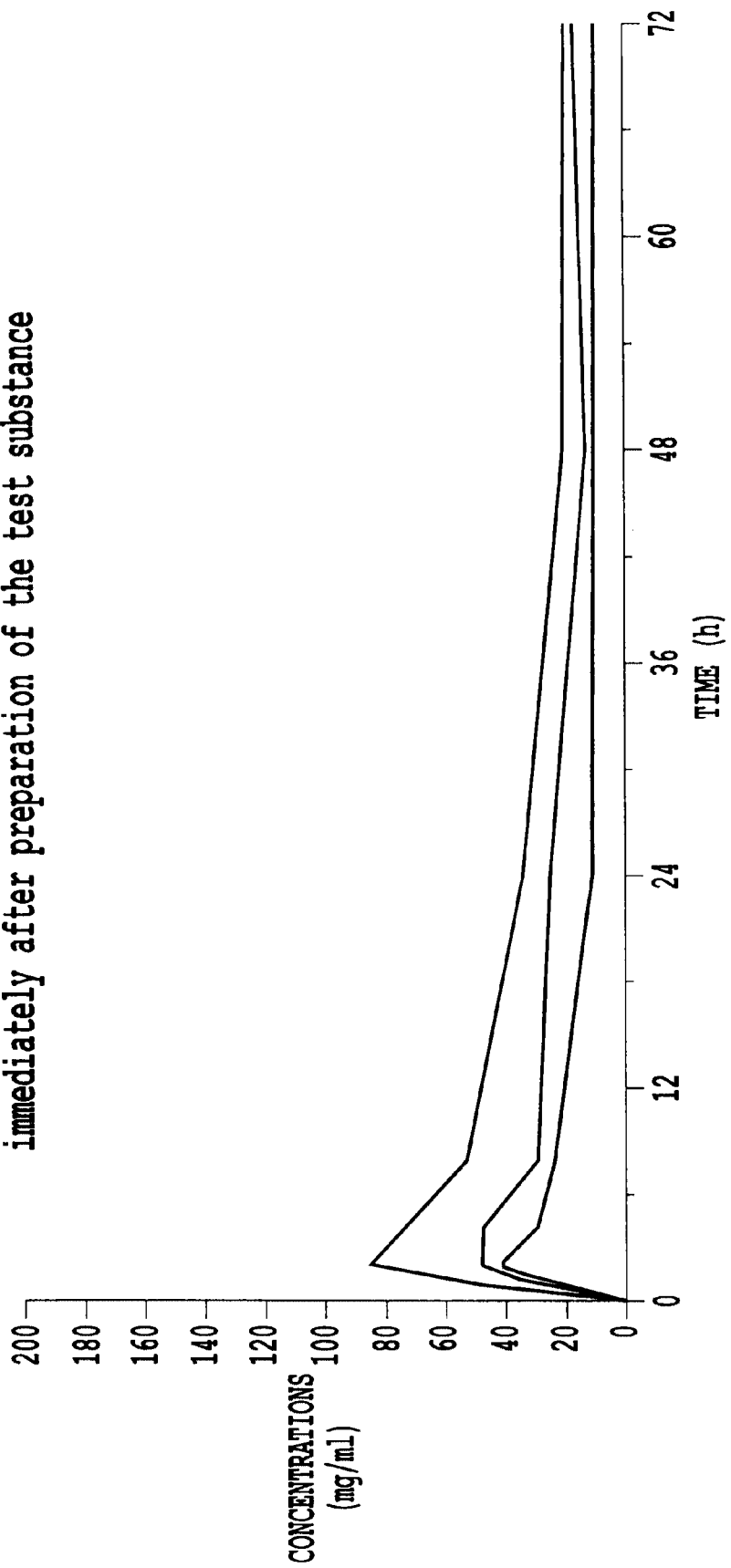
FIG. 4 shows the influence of the standing time after reconstitution on the plasma levels after s.c. injection; standing time=0 minutes, as described in Example 7. Plasma concentration of D-63153 after s.c. administration at 65 mg of D-63153 dissolved in 2.6 nl of in 2.6 ml of 0.1% (weight/volume) NaCl solution; immediately after preparation of the test compound. The test solution was administered s.c. to three dogs immediately and the three data sets in FIG. 4 represents the results for each of the three dogs.
Figure 5:
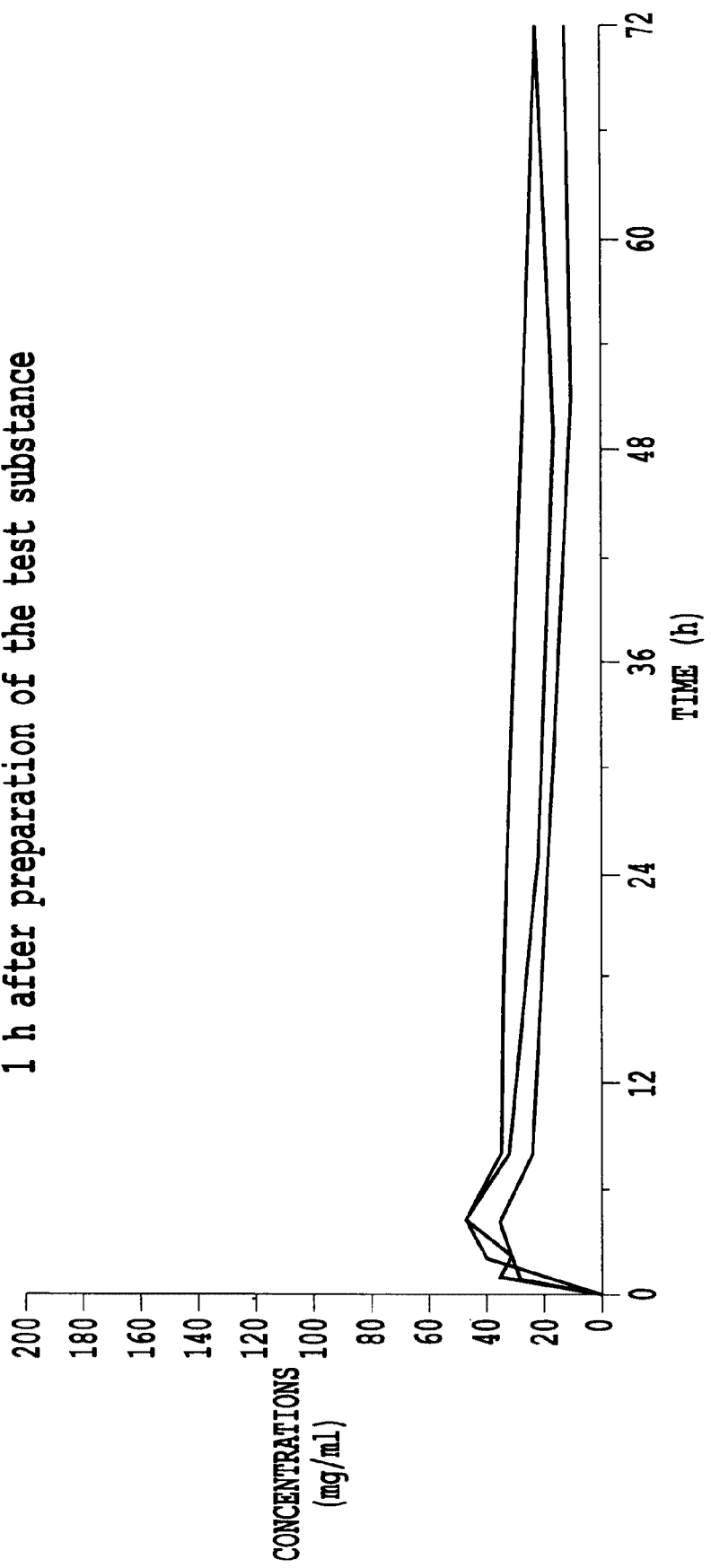
FIG. 5 shows the influence of the standing time after reconstitution on the plasma levels after s.c. injection; standing time=60 minutes, as described in Example 7. Plasma concentration of D-63153 after s.c. administration at 65 mg of D-63153 dissolved in 2.6 nl of in 2.6 ml of 0.1% (weight/volume) NaCl solution; 1 hour (60 minutes) after preparation of the test compound. The test solution was administered s.c. to three dogs after one hour and the three data sets in FIG. 5 represents the results for each of the three dogs.

Lyophilizates containing 65 mg of D-63153 were produced and reconstituted with 2.6 ml of a 0.1% strength NaCl solution, and the resulting solution was in one instance administered s.c. to dogs immediately (standing time: 0 minutes) (see FIG. 4) and in another instance administered s.c. (see FIG. 5) to dogs after one hour after reconstitution (standing time: 60 min). The D-63153 plasma levels were measured over a time of 72 hours.

The colloidal system obtained by aggregation changes during the standing time in that its viscosity increases. This is associated with a slight change in the plasma level plots, with the result that the maximum plasma concentration is reduced and the reproducibility of the plasma level plots is improved.

TABLE 1

(cf. example 2): Pharmacokinetic parameters of D-63153 non-depot administration form in beagle dogs, 1.68 mg/kg s.c. Pharmacokinetic parameters of D-63153

| D = 1.68 mg peptide base/kg n = 4 | D-63153 in 5.2% aqueous mannitol | | |
|---|---|---|---|
| | $C_{max}$ [ng/ml] | $t_{max}$ [h] | $AUC_{norm}$ [ng · h/ml] |
| Mean | 216.55 | 5.0 | 19434.3 |
| Min | 139.16 | 2.0 | 15458.0 |
| Max | 251.90 | 6.0 | 22103.8 |

TABLE 2

(cf. example 2): Pharmacokinetic parameters of D-63153
depot administration form in beagle dogs, 1.68 mg/kg s.c.
Pharmacokinetic parameters of D-63153

| D = 1.68 mg peptide base/kg n = 4 | D-63153 in 5.2% aqueous mannitol/ 0.1% NaCl | | |
|---|---|---|---|
| | $C_{max}$ [ng/ml] | $t_{max}$ [h] | $AUC_{norm}$ [ng · h/ml] |
| Mean | 97.44 | 7.0 | 17688.2 |
| Min | 64.75 | 2.0 | 14445.6 |
| Max | 199.62 | 8.0 | 19676.9 |

TABLE 3

(cf. example 4): Pharmacokinetic parameters of D-63153: comparison
between non-depot and depot administration form in volunteer male
test subjects, 10 mg/person (0.14–0.17 mg/kg) i.m.

| Person | $c_{max}$ [ng/ml] | $t_{max}$ [h] | $t_{last}$ [h] | $AUC_{0-tlast}$ [ng*h/ml] | $AUC_{0-24}$ [ng*h/ml] | $AUC_{0-24}$ [%] | $t_{1/2}$ [h] | MRT [h] |
|---|---|---|---|---|---|---|---|---|
| n | 6 | 6 | 6 | 6 | 6 | 6 | 6 | 6 |
| Non-depot | 99.90 | 0.50 | 300.00 | 1165.93 | 495.41 | 42.40 | 27.60 | 52.24 |
| Depot | 11.02 | 2.50 | 360.00 | 887.44 | 151.05 | 16.7 | 50.05 | 129.36 |

The invention claimed is:

1. A pharmaceutical gel preparation comprising a mixture of:
   (a) D-63153 or a pharmaceutically active salt thereof in lyophilized form at a concentration of from 5 to 50 mg of peptide per ml of the preparation, and
   (b) an aqueous solution of sodium chloride at a concentration of from 0.05% to 0.2% (weight/volume), and
   wherein the preparation is suitable for administration after reconstitution of (a) by the mixing of (a) and (b) and after a standing time of up to about 120 minutes subsequent to the mixing of (a) and (b).

2. The pharmaceutical preparation as claimed in claim 1 wherein the pharmaceutical gel preparation further comprises at least one pharmaceutically active ionic peptide compound selected from the group consisting of cetrorelix, teverelix, abarelix, ganirelix, azaline B, antide, detirelix, ramorelix, degarelix, or their pharmaceutically active salt and mixtures thereof.

3. The pharmaceutical preparation as claimed in claim 1 wherein D-63153 is a pharmaceutically active salt.

4. The pharmaceutical preparation as claimed in claim 1 wherein said aqueous solution further comprises an aqueous inorganic salt or acetic acid salt selected from the group consisting of calcium chloride, magnesium chloride, sodium acetate, calcium acetate, magnesium acetate and mixtures thereof.

5. The pharmaceutical preparation as claimed in claim 1 wherein the mixture is a liquid suspension or a semisolid dispersion.

6. The pharmaceutical preparation as claimed in claim 1 wherein the concentration of D-63153 is in the range from about 10 to about 50 mg per ml of the total amount of the pharmaceutical preparation.

7. The pharmaceutical preparation as claimed in claim 1 wherein the concentration of D-63153 is in the range from about 20 to about 30 mg per ml of the total amount of the pharmaceutical preparation.

8. The pharmaceutical preparation as claimed in claim 1 wherein the concentration of D-63153 is in the region of about 25 mg per ml of the total amount of the pharmaceutical preparation.

9. The pharmaceutical preparation as claimed in claim 1 wherein the concentration of sodium chloride ranges from 0.1% to 0.2% (weight/volume).

10. The pharmaceutical preparation as claimed in claim 1 wherein the concentration of sodium chloride is about 0.1% (weight/volume).

11. The pharmaceutical preparation as claimed in claim 1 wherein the concentration of D-63153 is about 25 mg per ml of the preparation, and the concentration of sodium chloride is about 0.1% (weight/volume).

12. A method for producing a pharmaceutical gel preparation as claimed in claim 1 comprising
   A) bringing together said D-63153 in lyophilized form and said aqueous solution and
   B) mixing the components.

13. The method for producing a pharmaceutical preparation as claimed in claim 12, wherein the concentration of D-63153 is about 25 mg/ml, and the concentration of sodium chloride is about 0.1% (weight/volume).

14. The method for producing a pharmaceutical preparation as claimed in claim 12, further comprising sterilizing the peptide formulation by irradiation with gamma rays or electron beams.

15. The method for producing a pharmaceutical preparation as claimed in claim 12, where the production of (a) takes place with use of aseptic procedures.

16. A kit for producing a pharmaceutical gel preparation as claimed in claim 1, comprising from 5 to 50 mg per ml of the finished preparation of D-63153 in lyophilized form and an aqueous solution of an inorganic or acetic acid salt at a concentration of from 0.05% to 0.2% (weight/volume).

17. The kit as claimed in claim 16, wherein the D-63153 lyophilizate additionally comprises mannitol.

18. The kit as claimed in claim 16 wherein the concentration of D-63153 is about 25 mg per finished preparation and the concentration of the aqueous sodium chloride solution is about 0.1% weight/volume.

19. A method for treating a patient with D-63153, wherein a pharmaceutical preparation as claimed in claim 1 is administered subcutaneously or intramuscularly to the patient.

20. The method as claimed in claim 19 wherein the administered pharmaceutical preparation displays a sustained pharmaceutical activity.

21. The method as claimed in claim 19 wherein the administered pharmaceutical preparation displays a sustained pharmaceutical activity for at least 4 weeks.

22. The method as claimed in claim 19 wherein the administered pharmaceutical preparation displays a sustained pharmaceutical activity for at least 8 weeks.

23. The method as claimed in claim 19 wherein the administered pharmaceutical preparation displays a sustained pharmaceutical activity for at least 12 weeks.

24. A method for treating a hormone-dependent disorder in a patient by subcutaneous or intramuscular administration of a pharmaceutical preparation as claimed in claim 1 in a patient need thereof.

25. A method for treating prostate cancer in a patient by subcutaneous or intramuscular administration of a pharmaceutical preparation as claimed in claim 1 in a patient need thereof.

26. A method for treating breast cancer in a patient by subcutaneous or intramuscular administration of a pharmaceutical preparation as claimed in claim 1 in a patient need thereof.

27. A method for treating uterine myomas in a patient by subcutaneous or intramuscular administration of a pharmaceutical preparation as claimed in claim 1 in a patient need thereof.

28. A method for treating endometriosis in a patient by subcutaneous or intramuscular administration of a pharmaceutical preparation as claimed in claim 1 in a patient need thereof.

29. A method for treating precocious puberty in a patient by subcutaneous or intramuscular administration of a pharmaceutical preparation as claimed in claim 1 in a patient need thereof.

30. A method for modifying the reproductive function in a patient by subcutaneous or intramuscular administration of a pharmaceutical preparation as claimed in claim 1 in a patient need thereof.

31. The pharmaceutical preparation as claimed in claim 1 wherein the mixture is a molecular-dispersed or colloidal mixture which may be of liquid to semisolid consistency.

32. The pharmaceutical preparation as claimed in claim 1 wherein a colloidal dispersion is formed by reconstitution.

33. The pharmaceutical preparation as claimed in claim 1 wherein a colloidal dispersion is formed by storage or leaving to stand after reconstitution and changes its viscosity as a function of time and thus improves the reproducibility of the delayed release of active ingredient.

* * * * *